United States Patent [19]

Köppe et al.

[11] 4,119,728

[45] Oct. 10, 1978

[54] 1-PHENOXY-2-HYDROXY-3-ALKYNYLAMINO-PROPANES AND SALTS THEREOF AND TREATMENT OF CORONARY DISEASES THEREWITH

[75] Inventors: Herbert Köppe; Werner Kummer; Helmut Stähle; Gojko Muacevic, all of Ingelheim am Rhein, Fed. Rep. of Germany

[73] Assignee: Boehringer Ingelheim GmbH, Ingelheim am Rhein, Fed. Rep. of Germany

[21] Appl. No.: 742,782

[22] Filed: Nov. 18, 1976

Related U.S. Application Data

[63] Continuation-in-part of Ser. No. 609,998, Sep. 3, 1975, Pat. No. 4,016,202, which is a continuation-in-part of Ser. No. 444,713, Feb. 22, 1974, Pat. No. 3,925,446.

[30] Foreign Application Priority Data

Feb. 28, 1973 [DE] Fed. Rep. of Germany ....... 2309887
Jan. 26, 1974 [DE] Fed. Rep. of Germany ....... 2403809

[51] Int. Cl.$^2$ .................. A61K 31/165; C07C 103/10
[52] U.S. Cl. ................................ 424/324; 260/562 A
[58] Field of Search .................... 260/562 A; 424/324

[56] References Cited

U.S. PATENT DOCUMENTS

| 3,574,749 | 4/1971 | Howe et al. ............. 260/562 A |
| 3,839,446 | 10/1974 | Teach .................... 260/562 A |
| 3,852,468 | 12/1974 | Howe et al. ............. 260/562 A |
| 3,872,147 | 3/1975 | Köppe et al. ............ 260/562 A |
| 4,041,075 | 8/1977 | Smith .................... 260/562 A |

Primary Examiner—Stanley J. Friedman
Attorney, Agent, or Firm—Hammond & Littell

[57] ABSTRACT

Racemic and optically active compounds of the formula

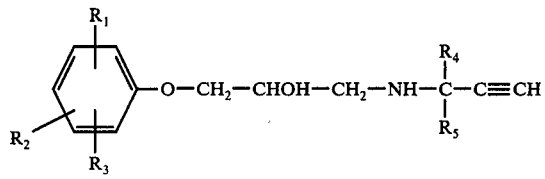

wherein
 $R_1$ is —COOR$_6$, where R$_6$ is hydrogen or alkyl of 1 to 4 carbon atoms; —OCO—R$_9$ or —NH—CO—R$_9$, where R$_9$ is alkyl of 1 to 6 carbon atoms, phenyl (alkyl of 1 to 4 carbon atoms) or phenyl; —Q—CO—NR$_7$R$_8$, where Q is a single bond, oxygen, —NH—, —CH$_2$— or —CH$_2$—NH—, and R$_7$ and R$_8$ are hydrogen, lower alkyl or, taken together with the nitrogen, pyrrolidino, piperidino or morpholino; cyano-phenyl; carboxylphenyl; cyano-phenoxy; or carboxyl-phenoxy;
 $R_2$ is hydrogen, halogen, alkyl of 1 to 4 carbon atoms, alkoxy of 1 to 4 carbon atoms, alkanoyl of 2 to 4 carbon atoms, alkenyl of 2 to 4 carbon atoms, amino, nitro or, together with R$_1$, 3,4-methylenedioxy;
 $R_3$ is hydrogen, halogen, alkyl of 1 to 4 carbon atoms, alkoxy of 1 to 4 carbon atoms or, together with R$_2$ in the ortho-position, —CH=CH—CH=CH— or —(CH$_2$)n— where $n$ is an integer from 3 to 5;
 $R_4$ is hydrogen or alkyl of 1 to 3 carbon atoms; and
 $R_5$ is alkyl of 1 to 3 carbon atoms or, together with R$_4$, —(CH$_2$)$_p$—, where $p$ is an integer from 4 to 6;
and physiologically compatible acid addition salts thereof. The compounds as well as their salts are useful as adrenolytics and hypotensives.

7 Claims, No Drawings

1-PHENOXY-2-HYDROXY-3-ALKYNYLAMINO-PROPANES AND SALTS THEREOF AND TREATMENT OF CORONARY DISEASES THEREWITH

This is a continuation-in-part of copending application Ser. No. 609,998 filed Sept. 3, 1975, now U.S. Pat. No. 4,016,202 granted Apr. 5, 1977; which in turn is a continuation-in-part of application Ser. No. 444,713 filed Feb. 22, 1974, now U.S. Pat. No. 3,925,446 granted Dec. 9, 1975.

This invention relates to novel 1-phenoxy-2-hydroxy-3-alkynylamino-propanes and acid addition salts thereof, as well as to various methods of preparing these compounds.

More particularly, the present invention relates to a novel class of racemic and optically active 1-phenoxy-2-hydroxy-3-alkynylamino-propanes represented by the formula

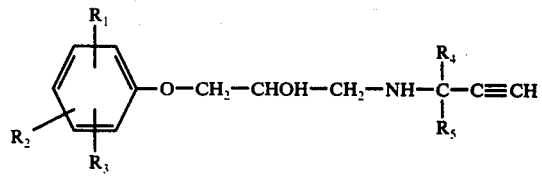

wherein
  $R_1$ is —$COOR_6$ where $R_6$ is hydrogen or alkyl of 1 to 4 carbon atoms; —OCO—$R_9$ or —NH—CO—$R_9$, where $R_9$ is alkyl of 1 to 6 carbon atoms, phenyl (alkyl of 1 to 4 carbon atoms) or phenyl; —Q—CO—$NR_7R_8$, where Q is a single bond, oxygen, —NH—, —$CH_2$— or —$CH_2$—NH—, and $R_7$ and $R_8$ are hydrogen, lower alkyl or, taken together with the nitrogen, pyrrolidino, piperidino or morpholino; cyano-phenyl; carboxy-phenyl; cyano-phenoxy; or carboxyl-phenoxy;
  $R_2$ is hydrogen, halogen, alkyl of 1 to 4 carbon atoms, alkoxy of 1 to 4 carbon atoms, alkanoyl of 2 to 4 carbon atoms, alkenyl of 2 to 4 carbon atoms, amino, nitro or, together with $R_1$, 3,4-methylenedioxy;
  $R_3$ is hydrogen, halogen, alkyl of 1 to 4 carbon atoms, alkoxy of 1 to 4 carbon atoms or, together with $R_2$ in the ortho-position, —CH=CH—CH=CH— or $(CH_2)_n$—, where n is an integer from 3 to 5
  $R_4$ is hydrogen or alkyl of 1 to 3 carbon atoms; and
  $R_5$ is alkyl of 1 to 3 carbon atoms or, together with $R_4$, —$(CH_2)_p$—, where p is an integer from 4 to 6;
and physiologically compatible acid addition salts thereof.

If $R_1$ represents an acyloxy or acylamino group, the acyl moiety thereof is preferably a lower aliphatic acyl group, especially lower alkanoyl, such as the acetyl, propionyl, butyryl or isobutyryl; or an araliphatic acyl group, especially phenylalkanoyl, such as phenacetyl, which is optionally substituted at the phenyl with one or several halogen atoms, alkyl groups, nitro, cyano or carboxyl groups.

The novel compounds may be produced in a number of ways, of which the following are representative:
(a) Reacting a compound of the formula

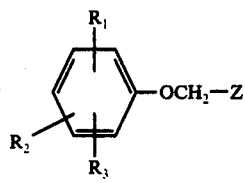

where $R_1$ to $R_3$ are defined as in formula I and Z is

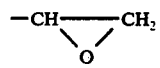

or —CHOH—$CH_2$—Hal (Hal = halogen), with an amine of the formula

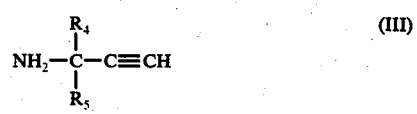

where $R_4$ and $R_5$ have the meanings indicated in formula I;

(b) Cleaving an easily removable protective group off compounds of the formula

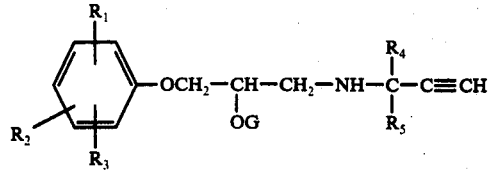

where $R_1$ to $R_5$ are defined as in formula I and G is an easily hydrogenolytically removable group, for example, an acyl or an acetal group.

(c) Cleaving a protective group off a compound of the formula

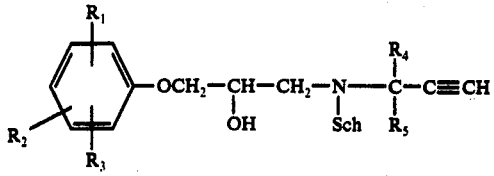

where $R_1$ to $R_5$ are defined as in formula I and Sch is an easily removable protective group, for example, an acyl group or the carbobenzoxy group;

(d) Hydrolyzing an oxazolidine derivative of the formula

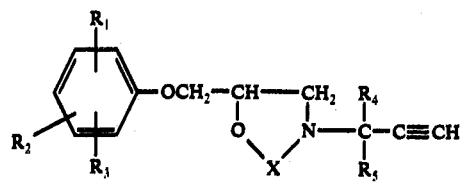

where $R_1$ to $R_5$ are defined as in formula 1, and X represents —CO—, —$CH_2$— or a —CH—lower alkyl group, for example, with sodium hydroxide or potassium hydroxide solution in water or in an alcohol/water mixture.

In addition, other processes for the production of compounds of formula I are possible, such as converting a compound having already the 3-alkynylaminopropanol-2 side chain, but not having one of the substituents $R_1$, $R_2$ or $R_3$ on the phenyl ring and in place thereof another substituent convertible to the desired substituent, to the desired substituent $R_1$, $R_2$, $R_3$ by conventional methods.

(e) Converting compounds of the formula

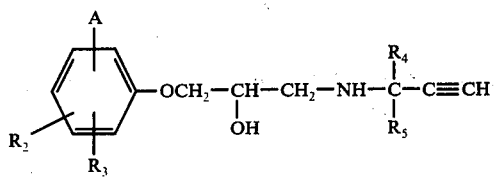
(VIIa)

where $R_2$ to $R_5$ are defined as in formula I and A is a group convertible by conventional methods, such as the $-CONH_2$ or $-COOR_6$ group (where $R_6$ is defined as in formula I), an alkoxy, O-acyl or $NO_2$ group, or compounds of the formula

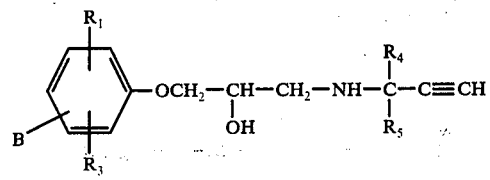
(VIIb)

where $R_1$ and $R_3$ to $R_5$ are defined as in formula I and B is a group convertible into $R_2$ by conventional methods, into compounds of the formula I, using the method required in each case (splitting off water, reducing, saponifying, cleaving an ether, alkylating).

Furthermore, the following process is suitable for producing compounds of the formula I, where $R_2$ or $R_3$ is a halogen atom:

(f) Introducing a halogen atom into compounds of the formula

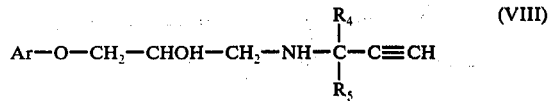
(VIII)

where $R_4$ and $R_5$ are defined as in formula I, and Ar is a group of the partial formula

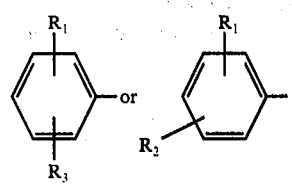
(IX)

(where $R_1$, $R_2$ and $R_3$ have the above meanings), for example, with a mixture of hydrogen halide and hydrogen peroxide at elevated temperature.

Some of the starting compounds required for carrying out the processes (a) to (f) are known. The remainder can be obtained by known processes. Thus, the epoxides of the formula II may be produced easily by reaction with a corresponding phenol or phenolate of the formula

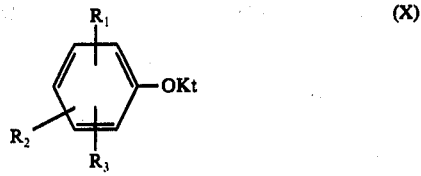
(X)

where $R_1$ to $R_3$ have the meanings mentioned above and Kt is hydrogen or a cation (e.g., an alkali metal cation). The epoxides may be used for production of further starting materials; for instance, the halohydrins of the formula II may be produced by reacting the epoxides with the corresponding hydrogen halide.

Amines of the formula III are known and represent mostly commercial products. Compounds of the formula IV may be obtained by reacting a halohydrin of the formula II with a compound (such as vinyl ether or dihydropyran) to give the protective group G, and subsequently reacting the obtained compound of the formula

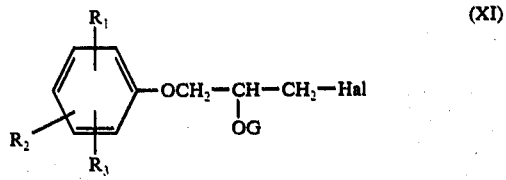
(XI)

with a compound of the formula III.

The tertiary amines of the formula V are obtained by reacting a compound of the formula X with a compound of the formula

(XII)

where $R_4$, $R_5$ and Sch have the above-mentioned meanings and Z is halogen.

The oxazolidinones of the formula VI (i.e., compounds where X = CO) are producible, for example, starting from the epoxides of the formula II, by reacting the latter with a urethane (producible from a chloroethyl formate and an amine of the formula II) of the formula

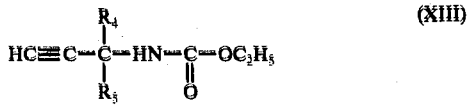
(XIII)

where $R_4$ and $R_5$ have the meanings mentioned above.

The compounds of the formulas VIIa, VIIb and VIII already contain the complete 1-phenoxy-2-hydroxy-3-alkynyl-amino-propane structure and may, therefore, be produced analogous to process (a) described above, starting from the corresponding phenol, via the corresponding 1-phenoxy-2,3-epoxypropane (producible by reaction with epichlorohydrin) by reaction with an alkynylamine of the formula III.

The compounds according to the invention possess an asymmetric carbon atom at the CHOH group and can occur, therefore, as racemates as well as in the form of optical antipodes. The latter may be obtained by separation of racemates with the conventional optically active acids, such as dibenzoyl- (or di-p-toluyl-)D-tartaric acid or D-3-bromocamphor-8-sulfonic acid or by using optically active starting materials as well.

The 1-aryloxy-2-hydroxy-3-alkynylamino-propanes of the formula I according to the invention may be converted into physiologically compatible acid addition salts thereof in the conventional way. Suitable acids are, for example, hydrochloric acid, hydrobromic acid, sulfuric acid, methane-sulfonic acid, maleic acid, acetic acid, oxalic acid, lactic acid, tartaric acid or 8-chlorotheophylline.

The compounds of the formula I and the physiologically compatible acid addition salts thereof have shown valuable therapeutic properties, in particular, adrenolytic properties as demonstrated by animal tests in guinea pigs and may, therefore, be used for treatment of prophylaxis of diseases of the coronaries and for treatment of cardiac arrhythmia, especially of tachycardia, in human medicine. The blood-pressure decreasing properties of the compounds are therapeutically interesting too. Compared to the known β-receptor blockers, for example, the commercial product 1(1-naphthyloxy)-2-hydroxy-3-isopropylaminopropane (Propranolol), the compounds have the advantage of a considerably decreased toxicity combined with a superior action.

The invention, therefore, also relates to a process for the treatment of coronary diseases, cardiac arrhythmia and high blood pressure in warm-blooded animals comprising administering a safe but effective amount of the 1-aryloxy-2-hydroxy-3-alkynylamino-propane compounds of the formula I.

Hence, particularly those compounds of the formula I have proved to be valuable, where $R_4$ and $R_5$ represent each a methyl group.

A further preferred sub-group is formed by those compounds of the formula I, where $R_1$ represents an acylamino group, especially acetylamino, and $R_2$ and $R_3$ are hydrogen, halogen or lower alkyl. $R_4$ and $R_5$ are again preferably methyl.

The single dose of the compounds according to the invention lies at 1 to 300 mgm preferably 5 to 100 mgm (orally) or 1 to 20 mgm (parenterally). When administered to warm-blooded animals, the single dosage range is from 0.015 to 5 mgm/kg.

The active ingredients according to the invention may be incorporated into the conventional galenic forms of administration, such as tablets, coated tablets, solutions, emulsions, powders, capsules or forms of sustained release. For the production of the above, the usual pharmaceutical excipients as well as the conventional methods of production may be applied.

Corresponding tablets may be obtained by mixing the active ingredients with known excipients, for example, with inert diluents, such as calcium carbonate, calcium phosphate or lactose, disintegrants, such as corn starch or alginic acid, binders, such as starch or gelatin, lubricants, such as magnesium stearate or talc and/or agents for obtaining sustained release, such as carboxypolymethylene, carboxymethylcellulose, cellulose acetate/phthalate or polyvinyl-acetate.

The tablets may also be composed of several layers. There may be produced correspondingly coated tablets by means of coating cores, prepared analogous to the tablets, with agents usually applied for tablet-coats, such as polyvinyl-pyrrolidone or shellac, gum arabic, talc, titanium dioxide or sugar. For obtaining sustained release or in order to avoid incompatibilities, the core may consist of several layers as well. Thus, the tablet coat for obtaining sustained release may also consist of several layers, whereby the excipients mentioned above for tablets may be used.

Potable solutions of the active ingredients or active ingredient combinations according to the invention may additionally contain a sweetener, such as saccharin, cyclamate, glycerin or sugar, as well as an agent improving the taste for example, a flavor, such as vanilla or orange extract. Besides they may comprise suspension auxiliaries or thickeners, such as sodium carboxymethylcellulose, wetting agents, such as condensation products of fatty alcohols with ethylene oxide, or protective substances, such as p-hydroxybenzoates.

Injectable solutions are produced in the conventional way, such as under addition of preservation agents, such as p-hydroxybenzoates, or stabilizers, such as "Komplexonen" (the sodium salt of ethylene diaminetetraacetic acid), and filled into injection vials or ampules.

Capsules containing the active ingredients or active ingredient combinations may be produced, for example, by admixing the active ingredients with inert carriers, such as lactose or sorbitol, and filling same into gelatin capsules.

Suitable suppositories may be produced by mixing the active ingredients or active ingredient combinations envisaged for same with conventional carriers, such as neutral fats or polyoxyethyleneglycol or its derivatives.

The compounds of the invention are suitable as well for combination with other pharmacodynamically active substances, such as, for example, coronary dilatators, sympathicomimetics, cardiac glycosides or tranquilizers.

The following examples illustrate the invention without restricting same in any manner.

EXAMPLE 1

1-α-Naphthoxy-3-(3-ethylpentynyl-4-amino-3)-2-propanol . HCl (according to process [a]) (I, $R_1 = H$, $R_2 + R_3 = -CH=CH-CH=CH-$, $R_4$ and $R_5 = C_2H_5$)

10 grams (0.05 mol) of 1-α-naphthoxy-2,3-epoxy-propane were dissolved in 80 ml of ethanol. 5.55 grams (0.05 mol) of 3-ethyl-3-amine-pentyne-4 were added and the mixture was refluxed for two hours at boiling temperature. After having cooled off, the solvent was distilled off. The residue was dissolved in ether and acidified with alcoholic HCl. The crystallizable compound was isolated and recrystallized from a mixture of acetonitrile and ethanol. Yield: 9.5 gm, m.p. 195° to 196° C.

EXAMPLE 2

1-m-Tolyloxy-3-(2-methylbutynyl-3-amino-2)-2-propanol . HCl (according to process [a]) (I, $R_1 = $ 3—$CH_3$, $R_2$ and $R_3 = H$, $R_4$ and $R_5 = CH_3$)

8.2 grams (0.05 mol) of 1-m-tolyloxy-2,3-epoxy-propane were dissolved in 90 ml of ethanol, and after addition of 6.25 gm (0.075 mol) of 2-methyl-2-aminobutyne-3, the mixture was refluxed for two hours. After distilling off the solvent, the residue was recrystallized from ethyl acetate under addition of petroleum ether. The crystalline base was dissolved in acetonitrile; alcoholic HCl was added and crystallization was started under addition of ether. 6.5 grams of colorless crystals were obtained, which are chromatographically pure. M.p. 139° to 141° C.

EXAMPLE 3

1-(2-Allylphenoxy)-3-(2-methylbutynyl-3-amino-2)-2-propanol oxalate (according to process [a]) (I, $R_1$ = 2-allyl, $R_2$ and $R_3$ = H, $R_4$ and $R_5$ = $CH_3$)

9.5 grams (0.05 mol) of 1-(2-allylphenoxy)-2,3-epoxy-propane were dissolved in 60 ml of methanol. 8.3 gm (0.1 mol) of 2-methyl-2-amino-butyne-3 were added and the mixture was refluxed for three hours. After having distilled off the solvent, the basic residue was dissolved in acetone and a solution of 6 gm of oxalic acid were added. The precipitating crystalline oxalate was recrystallized from acetone once more. Yield: 4.7 gm, m.p. 144° to 146° C.

Analogous to the Examples 1 to 3, the following compounds of the formula I were prepared by process (a), i.e. by reacting a correspondingly substituted 1-phenoxy-2,3-epoxypropane of the formula II with a corresponding amine of the formula III in ethanol.

TABLE

| $R_1$ | $R_2$ | $R_3$ | $R_4$ | $R_5$ | M.P. of HCl-Salt in Case Nothing Else Indicated ° C |
|---|---|---|---|---|---|
| 4-NH—CO—$NHCH_3$ | H | H | $CH_3$ | $CH_3$ | 107–109 (Base) |
| 4-NH—CO—$N(C_2H_5)2$ | H | H | $CH_3$ | $CH_3$ | 125–127 |
| 4-$CH_2$—CO—$NH_2$ | H | H | $CH_3$ | $CH_3$ | 107–110 (Base) |
| 4-COOH | H | H | $CH_3$ | $CH_3$ | 159–162 |
| 4-NH—$COCH_3$ | H | H | $CH_3$ | $CH_3$ | 137–138 (Base) |
| 2-$CONH_2$ | H | H | $CH_3$ | $CH_3$ | 230–233 |

EXAMPLE 4

1-(4-Hydroxycarbonylphenoxy)-3-(2-methylbutynyl-3-amino-2)-2-propanol . HCl (according to process [e]) (I, $R_1$ = —COOH, $R_2$ and $R_3$ = H, $R_4$ and $R_5$ = $CH_3$)

5 grams of 1-(4-ethoxycarbonylphenoxy)-3-(2-methyl-butynyl-3-amino-2)-2-propanol hydrochloride were refluxed in 30 ml of conc. HCl for two hours. After cooling, the crystalline mass that originated by hydrolysis was vacuum filtered and recrystallized twice from ethanol under addition of ether. Yield: 3.1 gm, m.p. 159° to 162° C.

EXAMPLES OF FORMULATIONS

| 1. | Tablets | | |
|---|---|---|---|
| | 1-(4-Carboxyphenoxy)-3-(2-methyl-butynyl-3-amino-2)-2-propanol . HCl | 40.0 | parts |
| | Corn starch | 164.0 | " |
| | Sec. calcium phosphate | 240.0 | " |
| | Magnesium stearate | 1.0 | " |
| | | 445.0 | parts |

Production:

The individual components were admixed well and the mixture was granulated in the usual way. The granulate was pressed into tablets of 445 mg by weight, of which each contains 40 mg of active ingredient.

| 2. | Gelatin Capsules | | |
|---|---|---|---|
| | The content of the capsules was composed as follows: | | |
| | 1-(4-Carboxyphenoxy)-3-(2-methylbutynyl-3-amino-2)-2-propanol . HCl | 25.0 | parts |
| | Corn starch | 175.0 | " |
| | | 200.0 | parts |

Production:

The active ingredients of the content of capsule were mixed well and 200 mgm portions of the mixture were filled into gelatin capsules of suitable size. Each capsule contains 25 mgm of the active ingredient.

| 3. | Injection Solution | | |
|---|---|---|---|
| | The solution was produced of the following ingredients: | | |
| | 1-(4-Carboxyphenoxy)-3-(2-methylbutynyl-3-amino-2)-2-propanol . HCl | 2.5 | parts |
| | Sodium salt of EDTA (ethylene-diamine-tetraacetic acid) | 0.2 | " |
| | Distilled water ad | 100.0 | " |

Production:

The active ingredient and EDTA-salt were dissolved in sufficient water and filled with water to the desired volume. The solution was filtered free from suspended particles and filled into ampules under aseptic conditions. Finally, the ampules were sterilized and sealed. Each ampule contains 25 mg of active ingredient.

| 4. | Coated Tablets with Sustained Release | | |
|---|---|---|---|
| Core: | | | |
| | 1-(4-Carboxyphenoxy)-3-(2-methylbutynyl-3-amino-2)-2-propanol . HCl | 25.0 | parts |
| | Carboxymethyl cellulose (CMC) | 295.0 | " |
| | Stearic acid | 20.0 | " |
| | Cellulose acetate/phthalate (CAP) | 40.0 | " |
| | | 380.0 | parts |

Production:

Active ingredient, CMC and stearic acid were mixed well and the mixture was granulated in the usual way, using a solution of the CAP in 200 ml of a mixture of ethanol/ethyl acetate. Then the granulate was pressed to 380 mgm cores, coated in the conventional way with a sugary 5% solution of polyvinylpyrrolidone in water. Each coated tablet contains 25 mgm of active ingredient.

| 5. | Tablets | | |
|---|---|---|---|
| | 1-(4-Carboxyphenoxy)-3-(2-methylbutynyl-3-amino-2)-2-propanol . HCl | 35.0 | gm |
| | 2,6-Bis-(diethanolamino)-4,8-dipiperi-dinopyrimido-[5,4-d]-pyrimidine | 75.0 | " |
| | Lactose | 164.0 | " |
| | Corn starch | 194.0 | " |
| | Colloidal silicic acid | 14.0 | " |
| | Polyvinylpyrrolidone | 6.0 | " |
| | Magnesium stearate | 2.0 | " |
| | Soluble starch | 10.0 | " |
| | | 500.0 | gm |

Production:

The active ingredient together with the lactose, corn starch, colloidal silicic acid and polyvinyl pyrrolidone was granulated after thorough mixing in the usual way, using an aqueous solution of the soluble starch. The granulate was admixed with the magnesium stearate and pressed into 1000 tablets each of 500 mgm of weight, containing each 35 mgm of the first and 75 mgm of the second active ingredient.

The preceding specific embodiments are illustrative of the practice of the invention. It is to be understood, however, that other expedients known to those skilled in the art or disclosed herein may be employed without departing from the spirit of the invention and the scope of the appended claims.

We claim:

1. A racemic or optically active compound of the formula

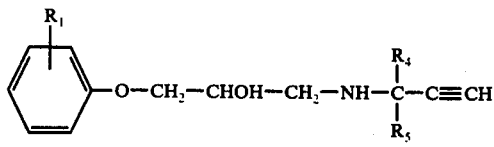

wherein
$R_1$ is —NH—CO—$R_9$, where $R_9$ is lower alkyl; or —Q—CO—$NR_7R_8$, where Q is single bond or —$CH_2$—, and $R_7$ and $R_8$ are each hydrogen or lower alkyl; and
$R_4$ and $R_5$ are each alkyl of 1 to 3 carbon atoms; or a physiologically compatible acid addition salt thereof.

2. A compound of claim 1, where
$R_1$ is —NH—CO—$R_9$, where $R_9$ is lower alkyl; and
$R_4$ and $R_5$ are each alkyl of 1 to 3 carbon atoms.

3. A compound of claim 2, where
$R_1$ is acetylamino; and
$R_4$ and $R_5$ are each alkyl of 1 to 3 carbon atoms.

4. A compound of claim 3, where
$R_1$ is acetylamino; and
$R_4$ and $R_5$ are methyl.

5. A compound of claim 1, where
$R_1$ is acetamido, and
$R_4$ and $R_5$ are methyl.

6. A pharmaceutical composition useful as an adrenolytic and hypotensive consisting essentially of an inert pharmaceutical carrier and an effective amount of a compound of claim 1.

7. The method of treating diseases of the coronaries in a warm-blooded animal, which comprises administering to said animal a safe but effective amount of a compound of claim 1.

* * * * *